(12) United States Patent
Warf, Jr. et al.

(10) Patent No.: US 7,887,850 B2
(45) Date of Patent: Feb. 15, 2011

(54) METHOD FOR REDUCING PATHOGENS IN THE GASTROINTESTINAL TRACT OF POULTRY AND OTHER FOOD ANIMALS

(75) Inventors: C. Cayce Warf, Jr., Woodinville, WA (US); G. Kere Kemp, Mercer Island, WA (US); John Richards, Redmond, WA (US)

(73) Assignee: Ecolab Inc., St. Paul, MN (US)

( * ) Notice: Subject to any disclaimer, the term of this patent is extended or adjusted under 35 U.S.C. 154(b) by 134 days.

(21) Appl. No.: 11/186,405

(22) Filed: Jul. 21, 2005

(65) Prior Publication Data

US 2006/0024405 A1  Feb. 2, 2006

Related U.S. Application Data

(60) Provisional application No. 60/590,714, filed on Jul. 23, 2004.

(51) Int. Cl.
  *A61K 33/14*  (2006.01)
  *A61P 31/04*  (2006.01)
(52) U.S. Cl. ....................... 424/661; 424/665
(58) Field of Classification Search ................. None
  See application file for complete search history.

(56) References Cited

U.S. PATENT DOCUMENTS

| | | | | |
|---|---|---|---|---|
| 5,100,652 | A * | 3/1992 | Kross et al. | 424/53 |
| 5,389,390 | A | 2/1995 | Kross | 426/332 |
| 5,830,511 | A | 11/1998 | Mullerat et al. | 424/661 |
| 6,063,425 | A | 5/2000 | Kross et al. | 426/335 |
| 6,475,527 | B1 | 11/2002 | Anderson et al. | 424/662 |
| 6,761,911 | B2 | 7/2004 | Anderson et al. | 424/662 |
| 2005/0232847 | A1 * | 10/2005 | Bromberg et al. | 423/473 |

OTHER PUBLICATIONS

STN online, file CABA, Acc. No. 94:49981, Doc. No. 19942205432 (Pardue et al., Poultry Science (1993), vol. 72, No. 2, p. 259-266), Abstract.*
STN online, file CAPLUS, Acc. No. 1996:289718, Doc. No. 124:341264 (Federal Register (1996), vol. 61, No. 79, pp. 17828-17829), Abstract.*
"Science Soundbites: Study Finds Sodium Chlorate Fed to Livestock Reduces Pathogens," *AMI Foundation News*, 4(2):3, Apr. 2002.
Anderson, R., et al., "Bactericidal Effect of Sodium Chlorate on *Escherichia coli* O157:H7 and *Salmonella* typhimurium DT104 in Rumen Contents in Vitro," *J Food Prot.*, 63(8):1038-42, Aug. 2000.
Anderson, R., et al., "Effect of Sodium Chlorate on *Salmonella* typhimurium Concentrations in the Weaned Pig Gut," *J Food Prot.*, 64(2):255-8, Feb. 2001.
Callaway, T., et al., "*Escherichia coli* O157:H7 Populations in Sheep can be Reduced by Chlorate Supplementation," *J Food Prot.*, 66(2):194-9, Feb. 2003.
Callaway, T., et al., "Effects of Sodium Chlorate on Antibiotic Resistance in *Escherichia coli* O157:H7," *Foodborne Pathog Dis.*, 1(1):59-63, Spring 2004.
McGraw, L., "Feeding Sodium Chlorate to Livestock to Kill *Salmonella* and *E. coli*," *Agricultural Research*, p. 19, Mar. 2001. URL: http://www.ars.usda.gov/is/AR/archive/mar01/sodium0301.pdf, 1 page.
Anderson et al., "Bactericidal Effect of Sodium Chlorate on *Escherichia coli* O157:H7 and *Salmonella* Typhimurium DT104 in Rumen Contents In Vitro," *Journal of Food Protection* 63(8): 1038-1042, 2000.
Pardue, S. L., and Jones, F. T., "Influence of a Novel Oxy-Halogen Compound on Early Growth and Nitrogen Retention of Broiler Chickens Challenged with *Salmonella*", 1993 Poultry Science 72:259-266.

* cited by examiner

*Primary Examiner*—Johann R Richter
*Assistant Examiner*—Frank I Choi
(74) *Attorney, Agent, or Firm*—Merchant & Gould P.C.

(57) ABSTRACT

A method for reducing pathogens in the gastrointestinal tract of a live animal comprising orally administering to the animal an effective amount of an aqueous antimicrobial solution, wherein the aqueous antimicrobial solution comprises from about 0.01% to about 0.1% by weight of a metal chlorite and a sufficient quantity of an acid having a first $pK_a$ of from about 2.0 to about 4.4 to adjust the pH of the aqueous antimicrobial solution to about 2.2 to about 4.5 and to maintain the chlorite ion concentration in the form of chlorous acid to not more than about 35% by weight of the total chlorite ion present in the aqueous antimicrobial solution, is disclosed.

10 Claims, No Drawings

METHOD FOR REDUCING PATHOGENS IN THE GASTROINTESTINAL TRACT OF POULTRY AND OTHER FOOD ANIMALS

CROSS-REFERENCE TO RELATED APPLICATION

This application claims the benefit under 35 U.S.C. §119 (e) of U.S. Provisional Patent Application No. 60/590,714 filed Jul. 23, 2004, which provisional application is incorporated herein by reference in its entirety.

BACKGROUND OF THE INVENTION

1. Field of the Invention

The present invention relates generally to a method for disinfecting poultry and other food animals, and, more particularly, to a method for reducing pathogens in the gastrointestinal tract of a live animal prior to slaughter.

2. Description of the Related Art

Fresh food animal products, including poultry, are susceptible to contamination by microorganisms that contact meat surfaces immediately after slaughter and evisceration, including organisms in the gastrointestinal tracts which can be transferred during processing. Contaminating microorganisms include bacteria such as *Salmonella* and *Campylobacter* species, *Listeria monocytogenes, Escherichia coli* and other coliforms, and other enteric organisms. Once bacteria such as *Salmonella* contact tissue surfaces, they rapidly attach and are difficult to remove even with chlorine disinfectant permitted for use in poultry sprays and chill tanks. In beef processing, for example, a particularly virulent strain of *E. coli*, denoted O157:H7, reportedly contaminated hamburger meat sold by a fast-food chain and caused several deaths in the U.S. in 1993. Food poisoning from other The problems created by *Salmonella* bacteria in poultry products are particularly noteworthy. Currently, Americans spend approximately $20 billion annually on poultry products, consuming about 80 pounds per capita. Approximately 35% to 45% of poultry reaching U.S. consumers is contaminated with *Salmonella* species. Improper cooking and physical transfer of the bacteria to food handling surfaces and thereafter to other foods result in the spread of the microorganisms, causing gastrointestinal disorders and, in some cases, death.

Breeders, hatcheries, feed ingredient suppliers, farms, processors, and distributors have all been implicated as contributors to *Salmonella* contamination in chickens and turkeys (Villarreal, M. E., et al., *J. Food Protection* 53: 465-467 (1990)). Contamination of but a few birds can lead to broader range contamination of other birds and cross-contamination to carcasses. Bacterial proliferation and other signs of spoilage can be delayed by refrigeration, but there is a limit to the degree of refrigeration that can be imposed on meat products, short of freezing the meat, and some bacteria such as psychrophiles can survive and even flourish at temperatures approaching the freezing point. It is thus preferable to control and destroy *Salmonella* and other microbial contaminants during processing to reduce the initial number of organisms on the meat.

Poultry processing is similar to the processing of other meat animals. Briefly summarized, caged birds arrive by truck at the processing plant. Typically, the birds are not fed for at least one to four hours before slaughter to allow the bird's intestinal tract to clear, thereby lowering the risk of fecal contamination during subsequent processing. The birds are hung by their feet on shackles in a dressing line, stunned and bled via throat cuts. After bleeding and while still hung, the birds are scalded, plucked and transferred to an evisceration line, where they are manually or mechanically eviscerated, inspected and spray-washed. The spray may contain chlorine as a disinfecting agent. Historically, the last step of the process has been chilling in a chill tank, by movement through a counterflow of cold water. The carcasses must reach an internal temperature of 5° C. or below, which usually takes about 45 minutes to one hour in a typical many-thousand gallon tank. After reaching this temperature, the carcasses are packaged or further cut into parts, and refrigerated or frozen.

*Salmonella* and other organisms can survive the scalding process, which involves temperatures of about 50° C. to 58° C. Though cross-contamination can occur during any stage of processing, the major problems arise during and after evisceration when microorganisms are freed from the intestinal tract and transferred to other tissue surfaces. When carcasses are placed in the chill tank, organisms and unremoved viscera and visceral contents enter the water and can come in contact with other carcasses.

The U.S.D.A. and F.D.A. allow the use of chlorine in the water, up to 50 parts per million (ppm), to destroy some of these organisms. Upper range chlorine levels transfer to the air and can irritate factory workers, so lower levels, e.g., 20 ppm, are typically employed. This compromises antimicrobial effectiveness, as does organic matter and debris that accumulate in water and consume available chlorine. Indeed, even the upper allowable chlorine levels cannot eliminate or significantly reduce pathogenic organisms. In addition, chlorine in process waters has a tendency to react with a variety of organic materials, both from water and from poultry, to form a series of chloro-organic molecules, e.g., trihalomethanes and chloramines, that have been implicated as mutagens and carcinogens.

Chlorine dioxide, which is less reactive with water components such as ammonia and nitrogen compounds, has been considered as an alternative disinfectant to chlorine in poultry processing. Chlorine dioxide can significantly reduce *Salmonella* and other unwanted microbial contaminants of meat surfaces, and at levels in water which are approximately one-seventh of that required for chlorine to achieve comparable effects.

Though chlorine dioxide has also been found to react with fewer amino acids than does chlorine (3 rather than 18), there is increasing evidence that the reactions cause undesirable effects on poultry surfaces. For example, it has been observed that chlorine dioxide, at the 1.4 ppm level in chiller water, was effective in reducing many bacteria and caused no detectable off-flavors on treated broilers, but the skin of the chickens was lighter in color than control carcasses, and the normal pinkish-white appearance had changed to grayish-white. Use of chlorine dioxide was curtailed in poultry processing as a result of sporadic retail complaints about "bleached" or old-looking carcasses. Moreover, subsequent chlorine dioxide experiments resulted in periodic episodes of severely discolored (blue-black) birds and random poor bacteriocidal efficacy.

Irradiation was approved by the U.S. government as an alternative antimicrobial treatment. However, irradiation appeared to not be viable for most poultry processors due to the high capital plant cost, high operating costs, and the additional cost of transporting carcasses to such facilities. Irradiation may also pose occupational risks to poultry factory workers.

Regulatory authorities in the U.S. have also approved the use of acidified chlorite/chlorous acid antimicrobial solutions in chiller tanks, as well as the direct application of such solutions to the defeathered/eviscerated carcasses immediately prior to their immersion in the chiller tanks. This results in the destruction of surface pathogens on individual carcasses, thereby reducing or eliminating their numbers so that they cannot subsequently contaminate the chiller waters and other non-contaminated carcasses. The application of these chlorite/chlorous acid solutions may be either by separate immersion of each poultry carcass in the liquid germicide solution, or by spray application. Typically, when these solutions are used to disinfect the surfaces of red-meat carcasses, following evisceration, they are applied as sprays.

For example, the application of acidified chlorite/chlorous acid antimicrobial solutions, for removing bacteria from poultry and other meats is the subject of U.S. Pat. Nos. 5,389,390 and 6,063,425. More specifically, U.S. Pat. No. 5,389,390 discloses a method for disinfecting a meat carcass by application of an aqueous solution containing from about 0.001-0.2% of a metal chlorite and a sufficient quantity of an acid to adjust the pH of the aqueous solution to about 2.2-4.5 and to maintain the chlorite ion concentration in the form of chlorous acid to not more than about 35% by weight of the aqueous solution. U.S. Pat. No. 6,063,425 discloses a method for disinfecting a meat carcass by spray application of an aqueous solution containing from about 0.05-0.12% of a metal chlorite and a sufficient quantity of an acid having a first $pK_a$ of from about 2.0-4.4 to adjust the pH of the aqueous solution to about 2.2-4.5 and to maintain the chlorite ion concentration in the form of chlorous acid to not more than about 35% by weight of the aqueous solution, wherein the molar ratio of the acid to metal chlorite is at least equal to the first $pK_a$ of the acid multiplied by the grams/liter concentration of metal chlorite in the aqueous solution.

In addition, various pre-slaughter methods of controlling the amount of pathogens in the gut of a live animal have been approved, such as the use of competitive exclusion cultures and antibiotics. More recently, the oral administration of sodium chlorate solutions to live animals, particularly cattle, prior to slaughter to reduce the amount of certain pathogens in the gut, specifically E. coli and Salmonella, has been proposed (U.S. Pat. Nos. 6,475,527 and 6,761,911 to Anderson et al.; Anderson, R. C., et al., J. Food Protection 63: 1038-1042 (2000); Callaway, T. R., et al., J. Food Protection 66: 194-199 (2003); and Callaway T. R., et al., Foodborne Pathogens and Disease 1:59-63 (2004)). Similarly, U.S. Pat. No. 5,830,511 to Mullerat discloses the oral administration of pH-buffered, redox-stabilized compositions comprising halide and oxyhalide ions, such as a mixture of chlorite, chloride and chlorate ions, wherein the pH of the composition is in the range of 7.5-13. However, such chlorate solutions are only effective against certain pathogens, namely pathogens possessing respiratory nitrate reductases, and, accordingly, do not offer broad spectrum antimicrobial protection.

Accordingly, although there have been advances in the field, there remains a need for improved, effective and economical method for removing Campylobacter, Salmonella and other unwanted microorganisms from poultry and/or other food animals. The present invention addresses these needs and provides further related advantages.

BRIEF SUMMARY OF THE INVENTION

In brief, the present invention is directed to a method for disinfecting poultry and other food animals, and, more particularly, to a method for reducing pathogens in the gastrointestinal tract of a live animal prior to slaughter.

More specifically, the present invention provides a method for reducing pathogens in the gastrointestinal tract of a live animal comprising orally administering to the animal an effective amount of an aqueous antimicrobial solution, wherein the aqueous antimicrobial solution comprises from about 0.01% to about 0.1% by weight of a metal chlorite and a sufficient quantity of an acid having a first $pK_a$ of from about 2.0 to about 4.4 to adjust the pH of the aqueous antimicrobial solution to about 2.2 to about 4.5 and to maintain the chlorite ion concentration in the form of chlorous acid to not more than about 35% by weight of the total chlorite ion present in the aqueous antimicrobial solution.

In further, more specific, embodiments, the aqueous antimicrobial solution comprises from about 0.03% to about 0.04% by weight of the metal chlorite and/or the pH of the aqueous antimicrobial solution is from about 2.5 to about 2.7.

In other further, more specific, embodiments, the metal chlorite is sodium chlorite and/or the acid is citric acid or sodium acid sulfate.

The antimicrobial solution of the present invention may be orally administered to the animal as drinking water and may be orally administered to the animal prior to slaughter of the animal. For example, the antimicrobial solution may be orally administered to the animal over a period of 24 hours or five days prior to slaughter of the animal.

In a specific application, the live animal is poultry.

These and other aspects of the present invention will be evident upon reference to the following detailed description of the invention.

DETAILED DESCRIPTION OF THE INVENTION

As noted previously, the present invention is directed to a method for reducing pathogens, such as Campylobacter, Salmonella and E. coli, in the gastrointestinal tract of a live animal prior to slaughter. By reducing the level of enteric pathogens prior to slaughter, the risk of fecal and cross contamination, during subsequent post-slaughter processing steps may be reduced. Accordingly, the method of the present invention may be combined with presently employed decontamination methods, such as scalding, chilling and spraying or rinsing with steam, hot water and/or chemical solutions, to further remove unwanted microorganisms from meat carcasses.

The topical application of aqueous acidified chlorite/chlorous acid antimicrobial solutions for removing bacteria from the surface of meat carcasses was disclosed in U.S. Pat. Nos. 5,389,390 and 6,063,425 to Kross et al., which are incorporated herein by reference in their entireties. Furthermore, certain acidified sodium chlorite products (e.g., SANOVA®) have been approved by the F.D.A. (21 C.F.R. 173.325) as antimicrobial sprays and/or dips for the treatment of pre-chill poultry carcasses, parts and pieces, red meat carcasses, red meat trim, seafood, and raw agricultural commodities.

It has now been found that the pathogens in the gastrointestinal tract of a live animal, such as poultry, may be reduced by orally administering certain of the foregoing aqueous antimicrobial acidified chlorite/chlorous acid solutions to the animal. In particular, it has been found that aqueous antimicrobial solutions comprising from about 0.01% to about 0.1% by weight of a metal chlorite and a sufficient quantity of an acid having a first $pK_a$ of from about 2.0 to about 4.4 to adjust the pH of the aqueous antimicrobial solution to about 2.2 to about 4.5 and to maintain the chlorite ion concentration in the form of chlorous acid to not more than about 35% by weight of the total chlorite ion present in the aqueous antimicrobial solution are effective in this regard.

Alkali metal chlorites, such as sodium or potassium chlorite, or a mixture of the same may be used in the practice of this invention. For example, in one embodiment, the alkali metal chlorite is sodium chlorite. In some embodiments, the acid is selected such that it will not fully ionize upon dissolution in water, and is further limited to the group of acids in which no more than about 1 in 100 of its first ionizable acid groups will dissociate in aqueous solution. This corresponds to acids having a first $pK_a$ value of about 2 or higher, although acids of $pK_a$ values greater than about 5 are not appropriate for this application. Suitable acids for use in this invention include sodium acid sulfate, phosphoric acid, citric acid, lactic acid, malic acid, fumaric acid and acetic acid, or mixtures of the same.

The antimicrobial solutions of the present invention may be administered to an animal by adding the solution to, or replacing the solution for, the animal's regular drinking water supply. Such administration may occur prior to shipment of the animal to a slaughter facility or upon arrival of the animal at such facilities. The antimicrobial solutions may be administered over a period of time prior to slaughter, for example, over periods ranging from five days to 24 hours prior to slaughter.

Furthermore, the antimicrobial solutions are administered in an amount effective to reduce the level of pathogens in the gastrointestinal tract of an animal. In other words, an effective amount is defined herein as that amount which will significantly reduce or eliminate the level of pathogens, and/or reduce the incidence of infection by these pathogens, in a treated animal in comparison to untreated control animal. A reduction of incidence of infection may be demonstrated by a significant reduction in the number of animals infected or the severity or pathogenicity of infection, in comparison with untreated control animal. It is also understood that a reduction of incidence of infection may be demonstrated by a significant inhibition of intestinal, ruminal, or cecal colonization by the microorganism (as indicated by one or more of reducing pathogen shedding, reducing the average pathogen concentration, or lowering the percentage of animals colonized) in comparison with untreated controls. Suitable amounts may be readily determined by the practitioner skilled in the art, and will vary with the specific subject animal, its age, size, and physiological condition. Without being limited thereto, suitable doses should provide a concentration of chlorite ion which is greater than or equal to about 18 ppm within the lumen of the intestinal tract or gut of the treated animal. It is generally envisioned that control of pathogens in poultry may require lower concentrations of the chlorite ion in the gut of the animal, while ruminant animals such as cattle may require higher concentrations. However, the upper limit of the chlorite ion concentration may be much higher and will depend on the levels tolerated by the subject animal.

The following examples are provided for the purpose of illustration, not limitation. Those skilled in the art will recognize, or be able to ascertain through routine experimentation, numerous equivalents to the specific procedures described herein. Such equivalents are considered to be within the scope of the present invention.

EXAMPLES

Example 1

The tolerance of broilers to graded levels of sodium chlorite and citric acid administered in drinking water was evaluated. A total of 320 broilers (35 days of age) were randomly allocated to 64 pens (5 birds/pen). Water treatments consisted of 8 concentrations of sodium chlorite (0, 0.012, 0.03, 0.06, 0.12, 0.3, 0.6 and 1.2 percent by weight) and 8 concentrations of citric acid (0, 0.003, 0.01, 0.02, 0.04, 0.08, 0.18 and 0.4 percent by weight). All solutions were prepared and replaced twice a day, and all birds were given free access to the solutions. Water intake, feed consumption, weight gain, and mortality was monitored during the seven day experimental period.

No significant (P>0.05) differences were detected in mortality during the experiment. Citric acid levels of up to 0.4% did not affect live performance, whereas, sodium chlorite concentrations above 0.12% significantly lowered weight gain and feed consumption. Linear and quadratic responses to daily and 7-day water consumption was observed for graded levels of citric acid and sodium chlorite in the water. Overall, concentrations of up to 0.02% of citric acid stimulated water consumption and may have a positive effect on feed efficiency (P<0.05). Sodium chlorite concentrations beyond 0.06% negatively affected live performance and water intake (P<0.05).

Example 2

The in vivo efficacy of acidified sodium chlorite (ASC) solutions, prepared by combining sodium chlorite and either citric acid or sodium acid sulfate, was evaluated in broilers challenged with *Salmonella*. Two hundred and forty broilers (35 days of age) were randomly allocated to four Petersime batteries (5 birds/pen, 12 pens/battery). The study involved 12 treatments: one negative control (plain water-no challenge), one positive control (plain water-challenged), and ten ASC solutions—five concentrations (0, 150 ppm, 300 ppm, 600 ppm and 1200 ppm) of sodium chlorite, acidified to a pH of 2.6±0.1 with either citric acid or sodium acid sulfate. All birds, except for the controls, were fasted for two hours and orally gavaged with $10^4$ CFU/mL of *Salmonella Typhimurium* one hour before the initiation of treatments. The ASC solutions were freshly mixed and replaced every four hours over a period of 24 hours, and all birds were given free access to the solutions. Live performance (body weight, water consumption and weight gain/loss) was measured during the 24 hour experimental period. All 240 birds were then necropsied, the digestive tract was aseptically removed, split into 3 segments of upper (crop to gizzard), middle (duodenum to cecal junction) and lower (ceca to cloaca) for *Salmonella* enumeration (CFU/g).

No significant (P>0.05) changes were found in body weight, weight gain/loss and in the appearance/color of the excreta. There was no significant acidifier (citric acid or sodium acid sulfate) effect on water consumption or *Salmonella* counts. However, significant (P<0.05) concentration effect for ASC was detected, where levels beyond 600 ppm negatively affected water consumption. ASC reduced *Salmonella* in the upper segment of the digestive tract linearly (P<0.05) with increasing concentrations. Levels of ASC to reduce *Salmonella* in the middle and lower digestive tract segments were >600 and >1200 ppm, respectively.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

Furthermore, all of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

What is claimed is:

1. A method for reducing pathogens in the gastrointestinal tract of a live animal comprising orally administering to the animal an effective amount of an aqueous antimicrobial solution to reduce bacteria comprising *Campylobacter* and *Salmonella*, wherein the aqueous antimicrobial solution comprises from about 0.01% to about 0.1% by weight of a metal chlorite and a sufficient quantity of an acid having a first $pK_a$ of from about 2.0 to about 4.4 to adjust the pH of the aqueous antimicrobial solution to about 2.2 to about 4.5 and to maintain the chlorite ion concentration in the form of chlorous acid to not more than about 35% by weight of the total chlorite ion present in the aqueous antimicrobial solution.

2. The method of claim 1 wherein the aqueous antimicrobial solution comprises from about 0.03% to about 0.04% by weight of the metal chlorite.

3. The method of claim 1 wherein the pH of the aqueous antimicrobial solution is from about 2.5 to about 2.7.

4. The method of claim 1 wherein the metal chlorite is sodium chlorite.

5. The method of claim 1 wherein the acid is citric acid or sodium acid sulfate.

6. The method of claim 1 wherein the antimicrobial solution is orally administered to the animal as drinking water.

7. The method of claim 1 wherein the antimicrobial solution is orally administered to the animal prior to slaughter of the animal.

8. The method of claim 7 wherein the antimicrobial solution is orally administered to the animal over a period of 24 hours prior to slaughter of the animal.

9. The method of claim 7 wherein the antimicrobial solution is orally administered to the animal over a period of five days prior to slaughter of the animal.

10. The method of claim 1 wherein the animal is poultry.

* * * * *